United States Patent [19]

Firth et al.

[11] 4,111,658
[45] Sep. 5, 1978

[54] CATALYTIC GAS DETECTORS

[75] Inventors: Jack Graham Firth, St. Albans; Stephen John Gentry; Alan Jones, both of Sheffield, all of England

[73] Assignee: National Research Development Corporation, London, England

[21] Appl. No.: 858,403

[22] Filed: Dec. 7, 1977

[30] Foreign Application Priority Data

Dec. 13, 1976 [GB] United Kingdom ............... 51935/76

[51] Int. Cl.² ........................................... G01N 27/16
[52] U.S. Cl. ...................................... 23/232 E; 422/98
[58] Field of Search ............ 23/254 E, 232 E, 255 E; 338/34

[56] References Cited

U.S. PATENT DOCUMENTS

| 3,092,799 | 6/1963 | Baker | 23/254 E UX |
| 3,625,756 | 12/1971 | Taguchi | 23/254 E X |
| 3,644,795 | 2/1972 | Taguchi | 23/254 E UX |

*Primary Examiner*—Robert M. Reese
*Attorney, Agent, or Firm*—Cushman, Darby & Cushman

[57] ABSTRACT

A device sensitive to a combustible gas having an exothermic oxidation reaction comprises a catalytic element in the form of a body of material a major proportion of which consists of an aluminosilicate zeolite having a ratio of silicon to aluminum of greater than two and a three-dimensional pore structure; a catalyst metal within the zeolite pores; and heating means for heating the catalyst to temperatures at which it will cause combustion of the gas.

10 Claims, 2 Drawing Figures

U.S. Patent  Sept. 5, 1978  4,111,658
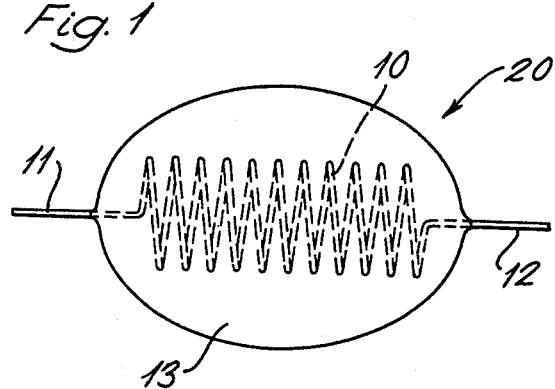
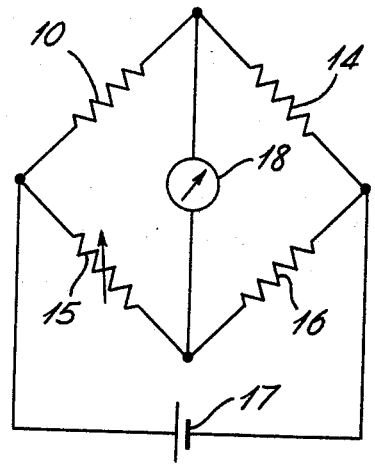

CATALYTIC GAS DETECTORS

This invention relates to catalytic gas detectors.

It is well known to detect the presence of a specific combustible gas in an oxygen-containing atmosphere by bringing the atmosphere into contact with a suitable catalyst maintained at a temperature at which it is capable of causing combustion of the specific gas, and sensing any thermal effect on the catalyst caused by the occurrence thereon of a combustion reaction. In an arrangement used for the detection of methane and disclosed in British Patent No. 892,530, the catalyst is in the form of a surface coating or impregnation of a pellet of refractory material within which is embedded a coil of wire used for heating the catalyst and for sensing the aforesaid thermal effect either by detecting changes in the resistance of the wire resulting from changes in the temperature of the pellet or by detecting changes in the magnitude of the heating current necessary to maintain the pellet at a given temperature.

It is also known that palladium can catalyse the oxidation of the combustible gas methane. Further, in 'Nature', volume 212, No. 5066, Dec. 3rd 1966, pages 1036 to 1037, in a paper by Firth and Holland, the catalytic oxidation of methane in the presence of palladium was studied, the palladium being supported by zeolite materials produced by the Linde Company under the designations 13X and 4A. Further studies were reported in 'Nature', volume 217, No. 5135 Mar. 30th 1968, pages 1252 to 1253. In 'Transactions of the Faraday Society', No. 559, volume 65 part 7, July 1969, pages 1891 to 1896, a study of the catalytic oxidation of methane on zeolites containing rhodium, iridium, palladium and platinum were reported.

In these three papers, it was realised that the metal catalyst was present within the pores of the zeolite material, that methane molecules were small enough to enter the pores, and that large molecules such as a silicone material, which may be a catalyst poison, could not enter the pores so that catalyst poisoning was avoided.

However, catalyst poisons can easily be excluded from a methane detector by passage of an atmosphere under test through active charcoal before it reaches the catalyst. It is therefore believed that no practical use has been made in respect of these studies in the field of gas detection. There is also the requirement to sense combustible gases other than methane, and further, the material of which such a catalytic element is made must be capable of withstanding elevated temperatures for long periods. The zeolites Linde type 13X and type 4A do not have good thermal stability.

According to the invention, a device sensitive to a combustible gas comprises a catalytic element in the form of a body of material a major proportion of which consists of an aluminosilicate zeolite having a ratio of silicon to aluminum of greater than 2 and a three dimensional pore structure; a catalyst metal which is present within the zeolite pores; and means for heating the catalyst to a temperature at which it will cause combustion of said gas. There may also be provided means for sensing any thermal effect on the catalyst caused by the occurrence thereon of the combustion reaction.

The zeolite may be either a naturally-occurring or a manmade material. It is an advantage of zeolites having a ratio of silicon to aluminum of greater than 2 that they have good thermal stability and can therefore operate at elevated temperatures for considerable periods.

In one form of the device the pore diameter of the zeolite is between 3 and 6 Angstrom units, preferably between 3.8 and 5.0 Angstrom units, and the device is sensitive to straightchain hydrocarbons having less than five carbon atoms. A suitable zeolite may be chabazite.

In another form of the device which may be sensitive to a wide range of gases, the pore diameter of the zeolite is between 6 and 9 Angstrom units and the device is sensitive to combustible gases having molecular diameters of less than 9A. Suitable zeolites are the Linde Company zeolites designated type Y, Omega and Ultrastable Y.

It is to be understood that in this specification the term combustible gas refers to a gas which has an exothermic oxidation reaction. The few gases, such as nitrogen and carbon dioxide, which do not have exothermic oxidation reactions cannot be detected by a device according to the invention.

The catalyst metal will always be chosen depending on the gas or gases to which the device is intended to be sensitive. The metal will usually be a metal in the Transition Groups of the Periodic Table, such as palladium, platinum, rhodium, iridium and copper, and will be in neutral or ionic form. In some cases the catalytic effect will in fact be due to an oxide of the metal formed during preparation or pre-treatment, such as conditioning, of the catalytic element.

The catalyst metal may be introduced into the pores of the zeolite material by a process including an ion-exchange step in which an ion, usually sodium, present in the zeolite material is exchanged for a catalyst metal ion present in a water-soluble salt. Alternatively, the catalyst metal may be deposited on the zeolite from a water-soluble salt of the required metal.

Usually the material of which the catalytic body is made will also contain an inactive binder, which may be present as 10 to 30 percent by weight of the catalytic element. Suitable binders are bentonite and "Attagel 50" (Registered Trade Name).

Also according to the invention, a method of detecting a combustible gas comprises exposing to an atmosphere to be tested a catalytic element in the form of a body of material a major proportion of which consists of an aluminosilicate zeolite having a ratio of silicon to aluminium of greater than 2 and a three dimensional pore structure, there being present within the zeolite pores a catalyst metal; maintaining the catalyst at a temperature at which it will cause the combustion of said combustible gas in an oxygen-containing atmosphere; and sensing any thermal effect on the catalyst caused by the occurrence thereon of the combustion reaction.

The invention will now be described by way of example with reference to the accompanying drawings in which:

FIG. 1 illustrates a gas sensitive element; and

FIG. 2 is a diagram of an electrical circuit in which the element may be used.

In FIG. 1 a catalytic element 20 according to the invention consists of a length of platinum wire whose central section is shaped to form a coil 10 with the free ends 11 and 12 of the wire extending parallel to the axis of the coil 10 so as to enable the coil to be readily connected in an electrical circuit. Typically the wire may have a diameter of 0.05 millimeters and the coil 10 may consist of eleven turns of pitch 0.125 millimeter and diameter 0.5 millimeter. The coil is embedded in a body of material 13 except for the free ends 11 and 12. The body of material comprises a mixture of a zeolite material, a binder and a catalyst material.

In the preparation of the catalytic element, the first step is to prepare a catalyst-loaded zeolite by one of two alternative methods, ion exchange and impregnation.

In an ion-exchange process, a Linde type Y zeolite is slurried in water and titrated with molar hydrochloric acid until the slurry is weakly acid with a pH of about 6. Tetrammine palladium nitrate $(NH_3)_4 Pd(NO_3)_2$ is dissolved in water and slowly added to the slurry in a quantity such that all of the sodium ions present in the zeolite will theoretically be exchanged for palladium ions. The mixture is stirred for 16 hours at room temperature, filtered, washed to remove exchanged sodium ions and dried at 350° C. for 4 hours.

In an alternative ion-exchange process, tetrammine palladium chloride $(NH_3)_4 Pd Cl_2$ is used instead of the nitrate.

In an impregnation process, the same procedure is followed but ammonium chlorpalladite solution is used instead of the tetrammine solution.

When palladium has been introduced into a zeolite by ion exchange, it is believed that the metal is chemically bound to the zeolite, and is in the form of palladium II ions. When an impregnation process is used, it is believed that the palladium is not chemically bound and is in metallic form.

Whichever method of preparation is used, it has been found that relatively little catalyst metal is present on the external surface of the zeolite; this is indicated by a small initial drop in sensitivity on exposure of the catalytic element in its final form to a catalyst poison.

In the next step in the preparation, the palladium-loaded zeolite is mixed with between 10 and 30% by weight of bentonite binder, and is slurried in water. The slurry is applied in drops to the coil of platinum wire and dried, either in hot air or by passing an electric current through the coil. Several applications may be needed to provide complete cover of the coil. The catalytic element is then "conditioned", typically by passing a current through the coil so that the element is maintained at 500° C, in air, for 30 minutes.

The coil 10 may be connected into a circuit such as a Wheatstone bridge circuit shown in basic form in FIG. 2. The coil 10 forms one arm of the bridge, the other three arms being constituted by a compensating resistor 14 having a resistance approximately equal to that of the coil 10, a variable resistor 15, and a fixed resistor 16 having a value such that the bridge can be balanced by adjustment of resistor 15. Across the two diagonals of the bridge are respectively connected a voltage source 17 and a current meter 18, the voltage of the source 17 being chosen so that the current passing through the coil 10 will be such as to heat the catalytic element 20 to a desired operating temperature when the bridge is balanced; resistor 14 will of course be heated to approximately the same temperature. The compensating resistor 14 may suitably be in the form of a coil of wire substantially identical to the coil 10 and embedded in an inert refractory material.

In use the catalytic element 20 and the compensating resistor 14 are heated to the required temperature and an atmosphere to be tested is brought into contact with them in a similar manner for the two devices; systems using gas flow or diffusion to effect such contact are well known in the art and therefore need not be described here. The bridge circuit is initially calibrated with the catalytic element 20 and the compensating resistor 14 in contact with air while heated to the desired operating temperature, and the bridge is balanced. The element 20 and resistor 14 are then exposed to an atmosphere under test. Any exothermic oxidation reaction taking place on the catalyst metal in the pores of the catalytic element 20 will cause a rise in temperature of the element, and a consequent change of resistance in the coil 10; the bridge circuit will no longer be balanced, and this condition will be indicated by the meter 18.

In an alternative arrangement, an electrical circuit is arranged to sense any change in the magnitude of the heating current necessary to maintain the catalytic element at a constant temperature. In yet another arrangement, as described in the complete specification of British Pat. No. 1,427,515, a discrete sample of an atmosphere under test is sealed into a reaction chamber containing the catalytic element 20 and compensating resistor 14, and the entire thermal effect on the catalyst body of any explosive gas in the sample is determined.

In whichever arrangement the catalytic element is used, suppose a catalytic element containing palladium is maintained at a temperature of 550° C, and exposed to an atmosphere containing methane gas. The methane molecules will penetrate to the palladium within the zeolite pores and an exothermic oxidation reaction will occur, raising the temperature of the element.

If the atmosphere also contains a larger molecule which may act as a catalyst poison, the large molecule cannot enter the pores and so catalyst poisoning is avoided.

Examples of the effect are given in Table I which sets out the times for a catalytic element to lose a proportion of its sensitivity in the presence of the catalyst poisons hexamethyl disiloxane and alkyl lead in petrol vapour. The effect on a "pellistor" type element, as described in UK Pat. No. 892,530, is compared with a Linde type Y zeolite containing palladium introduced by ion exchange and by impregnation.

TABLE I

| Catalyst Poison | Hexamethyl disiloxane (40 ppm) | Alkyl lead in Petrol vapour (0.5 ppm) |
| --- | --- | --- |
| Sensor | Time to lose ½ sensitivity (minutes) | Time to lose 10% sensitivity (hours) |
| Pellistor (palladium-thoria/alumina) | 0.5 (average of several readings) | 4 – 8 |
| Ion-exchanged Linde type Y zeolite | 500 *360 | 160 |
| Impregnated Linde type Y zeolite | 110 | 160 |

*life-tested before poisoning test.

It is clear from the Table that when the catalyst metal is contained within the pores of a Linde type Y zeolite material, the effect of a catalyst poison can be considerably delayed.

The response of the sensors was found to be directly proportional to hydrocarbon concentration below the lower explosive limit and independent of oxygen concentration over the range 10 to 60%. Typical sensitivity to methane in air was 25 millivolts percent.

We claim:

1. A device sensitive to a combustible gas having an exothermic oxidation reaction comprising a catalytic element in the form of a body of material a major proportion of which consists of an aluminosilicate zeolite having a ratio of silicon to aluminium of greater than two and a three dimensional pore structure; a catalyst metal within the zeolite pores; and heating means for heating the catalyst to a temperature at which it will cause combustion of the gas.

2. A device according to claim 1 in which the pore diameter of the zeolite is between 3 and 6 Angstrom units.

3. A device according to claim 2 in which the pore diameter of the zeolite is between 3.8 and 5.0 Angstrom units.

4. A device according to claim 1 in which the pore diameter of the zeolite is between 6 and 9 Angstrom units.

5. A device according to claim 4 in which the zeolite is selected from the group consisting of zeolites designated Type Y, Omega and Ultrastable Y.

6. A device according to claim 1 in which the catalyst metal is a metal in the Transition Groups of the Periodic Table.

7. A device according to claim 6 in which the catalyst metal is palladium.

8. Gas sensing apparatus including a gas-sensitive device according to claim 1 and further comprising sensing means arranged to sense any thermal effect on the catalyst caused by the occurrence thereon of the combustion reaction.

9. Gas sensing apparatus according to claim 8 comprising an electrical bridge circuit with the gas-sensitive device arranged in one arm thereof, the bridge being arranged to sense any change in the electrical resistance of the gas sensitive device.

10. A method of detecting a combustible gas having an exothermic oxidation reaction comprising exposing to an atmosphere to be tested a catalytic element in the form of a body of material a major proportion of which consists of an aluminosilicate zeolite having a ratio of silicon to aluminium of greater than 2 and a three dimensional pore structure, there being a catalyst metal within the zeolite pores; maintaining the catalyst at a temperature at which it causes combustion of said combustible gas in an oxygen-containing atmosphere; and sensing any thermal effect on the catalyst caused by the occurrence thereon of the combustion reaction.

* * * * *